US011164665B2

(12) United States Patent
Buckley et al.

(10) Patent No.: US 11,164,665 B2
(45) Date of Patent: Nov. 2, 2021

(54) VISUALIZING PATIENT CONDITIONS OVER TIME

(71) Applicant: CERNER INNOVATION, INC., Kansas City, KS (US)

(72) Inventors: Amanda Buckley, Victoria (CA); Rachel Lancaster, Victoria (CA); Emiliano Sune, Victoria (CA); Sarah Mundy, Victoria (CA)

(*) Notice: Subject to any disclaimer, the term of this patent is extended or adjusted under 35 U.S.C. 154(b) by 516 days.

(21) Appl. No.: 15/730,369

(22) Filed: Oct. 11, 2017

(65) Prior Publication Data
US 2018/0101651 A1    Apr. 12, 2018

Related U.S. Application Data

(60) Provisional application No. 62/406,775, filed on Oct. 11, 2016.

(51) Int. Cl.
  *G16H 15/00*    (2018.01)
  *G16H 70/20*    (2018.01)
  *G16H 50/70*    (2018.01)
  *G16H 30/20*    (2018.01)
  *G09B 23/28*    (2006.01)

(52) U.S. Cl.
  CPC .......... *G16H 15/00* (2018.01); *G16H 30/20* (2018.01); *G16H 50/70* (2018.01); *G16H 70/20* (2018.01); *G09B 23/28* (2013.01)

(58) Field of Classification Search
  CPC ..................................................... G16H 50/70
  See application file for complete search history.

(56) References Cited

U.S. PATENT DOCUMENTS

| | | | |
|---|---|---|---|
| 8,021,298 B2* | 9/2011 | Baird ................... | A61B 5/7475 600/300 |
| 2012/0065987 A1* | 3/2012 | Farooq .................. | G16H 40/20 705/2 |
| 2016/0148121 A1* | 5/2016 | Durham ................ | G16H 40/20 705/2 |
| 2018/0046763 A1* | 2/2018 | Price, Jr. .............. | G06F 16/148 |

* cited by examiner

*Primary Examiner* — Robert A Sorey
*Assistant Examiner* — Kristine K Rapillo
(74) *Attorney, Agent, or Firm* — Shook, Hardy & Bacon LLP

(57) ABSTRACT

Methods, computer-readable storage media, and systems for visually grouping related diagnoses and/or encounter/visit data together to provide treatment providers and patients with a summarized view of a patient's treatment per condition and how that treatment has changed over time are provided. Also provided are methods, computer-readable storage media, and systems for conflating related diagnoses and/or encounter data into a visual representation that summarizes a patient's treatment per condition and provides quickly discernible insight into how such treatment has changed over time.

20 Claims, 11 Drawing Sheets

VISUALIZING PATIENT CONDITIONS OVER TIME

CROSS-REFERENCE TO RELATED APPLICATIONS

This application claims priority under 35 U.S.C. § 120 to U.S. Provisional Patent Application No. 62/406,775, filed Oct. 11, 2016 and entitled "Visualizing Patient Encounters," which application is hereby incorporated by reference as if set forth in its entirety herein.

FIELD

The present embodiments relate to providing a visual representation that summarizes a patient's treatment history. More specifically, the present embodiments relate to conflating related diagnoses and/or encounter data into a visual representation that summarizes a patient's treatment per condition and provides quickly discernible insight into how such treatment has changed over time.

BACKGROUND

Patients often seek treatment for multiple conditions, which may or may not be related to one another, from multiple treatment providers and, frequently, multiple treatment facilities. When a patient presents for treatment, often it is difficult for a treatment provider to quickly and easily understand that patient's treatment history over time. This often leads to dissatisfaction among patients as they often feel as though each time they present to a particular treatment provider at a visit or encounter, it is as though the provider has never seen them before even though this quite often is not the case. Compounding patients' dissatisfaction is a feeling by patients that treatment providers are interested only in what is the matter with them rather than what matters to them. Given the intimate necessity of a provider-patient relationship and the vulnerability of patients as it relates to their health care treatment, better understanding a patient's priorities and history readily upon presentation could greatly benefit the provider-patient relationship and lead to more satisfactory and more productive treatment encounter experiences.

BRIEF SUMMARY

Aspects of the present technology described below include methods, computer-readable media, and systems for visually grouping related diagnoses and/or encounter/visit data together to provide treatment providers and patients with a summarized view of a patient's treatment per condition and how that treatment has changed over time. More specifically, aspects of the present technology relate to conflating related diagnoses and/or encounter data into a visual representation that summarizes a patient's treatment per condition and provides quickly discernible insight into how such treatment has changed over time.

Embodiments of the present invention are defined by the following claims, and nothing in this section should be taken as a limitation on those claims. Further aspects and advantages of embodiments of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of embodiments of the invention. Moreover, in the figures, like reference numerals designate corresponding parts throughout the different views.

FIG. 1 depicts an exemplary screen display illustrating encounter grouping indicators based on diagnoses and related information, in accordance with aspects hereof;

FIGS. 2-5 depict exemplary screen displays illustrating various encounter information associated with a particular encounter grouping indicator, in accordance with aspects hereof;

FIG. 7 depicts an exemplary screen display illustrating a "Patient Priority" selection area (e.g., box), in accordance with aspects hereof;

FIG. 8 depicts an exemplary screen display illustrating an encounter grouping indicator having a visual characteristic indicating that it has been selected as a priority of the subject patient, in accordance with aspects hereof;

DETAILED DESCRIPTION

Figure 6:
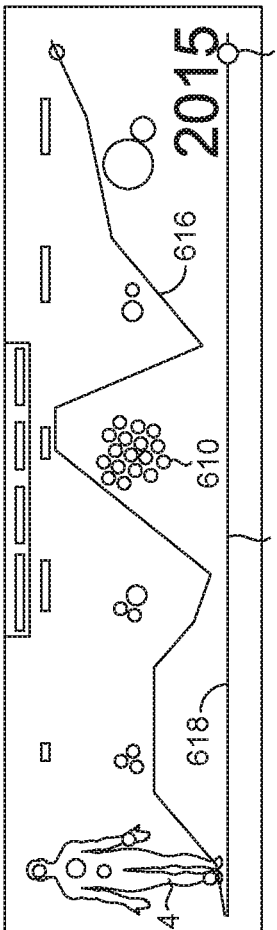
FIG. 6 depicts an exemplary screen display illustrating an exemplary body map and a trend line, in accordance with aspects hereof.

The subject matter herein is described with specificity to meet statutory requirements. However, the description itself is not intended to limit the scope of this patent. Rather, the inventors have contemplated that the claimed subject matter also might be embodied in other ways, to include different elements or combinations of elements similar to the ones described in this document, in conjunction with other present or future technologies.

Aspects hereof contemplate methods, systems, and computer-readable storage media that are effective for grouping related diagnosis and/or encounter data together to provide treatment providers and patients with a summarized view of a patient's treatment per condition and providing quickly discernible insight into how such treatment has changed over time. For example, it is contemplated that encounters having exact or related diagnoses associated therewith may be grouped together into one or more encounter groupings. It is further contemplated that each encounter grouping may be associated with an indicator that includes at least one visually discernible characteristic that is indicative of an attribute common amongst the encounters included in the encounter grouping. By way of example and not limitation, a visually discernible characteristic of an encounter grouping may be indicative of one or more of: a quantity of encounters associated with an exact, similar, or related diagnosis; a quantity of encounters associated with an encounter or treatment location; a quantity of encounters having a particular encounter type (e.g., hospitalization, outpatient clinical, etc.); or a quantity of encounters associated with a health-altering event (as defined from the perspective of the treatment provider or from the patient his or herself).

Aspects hereof contemplate that encounters having exact or related diagnoses associated therewith may be grouped together into one or more encounter groupings based upon a unified ontology or nomenclature system. Exemplary ontology or nomenclature systems include, by way of example only, the International Statistical Classification of Diseases and Related Health Problems (ICD) diagnosis codes, the Systemized Nomenclature of Medicine Clinical Terms (SNOMED) diagnosis codes, and/or diagnoses codes included in the Discern Ontologies service offered by Cerner Corporation. Aspects hereof further contemplate that encounter groupings may be associated with an indicator that includes at least one visually discernible characteristic that is indicative of an attribute common amongst the encounters included in the encounter grouping, and that the indicator may be presented in association with an interface. Aspects hereof additionally contemplate that the interface may take the form of a user interface operated by a software application or set of applications on a client computing device such as a personal computer, laptop, smart phone, or tablet computing device. In a particular exemplary aspect, the software application(s) may be included in the Power-Chart solution suite offered by Cerner Corporation.

Grouping and presenting patient encounters as contemplated by aspects hereof provides treatment providers with a way of visualizing groups of specific diagnoses (e.g., ICD-10 diagnoses) that are associated with a plurality of patient encounters occurring over a particular time period (e.g., the past twelve months or the lifetime of the patient) into more generic (and perhaps more colloquially-named) groups so that the treatment provider may be able to quickly and readily identify the primary condition (or conditions) for which the patient has been treated over the particular time period.

By way of example, contemplate a patient that has had five encounters over a twelve-month period of time. Further contemplate that the encounters are structured as follows: (1) One encounter having an Admitting Diagnosis of "Diabetes Mellitus Complicating Pregnancy" and a Discharge Diagnosis of "Diabetes Mellitus Complicating Pregnancy, Childbirth, or the Puerperium." The encounter is of the type "inpatient" indicating that the patient stayed at the treatment facility for at least twenty-four hours. (2) One encounter having a working diagnosis of "Diabetes Mellitus Type I," and a Reason for Visit Diagnosis of "Diabetes Mellitus Type 1 with Ketoacidosis." The encounter is of the type "outpatient" indicating that the patient stayed at the treatment facility for less than twenty-four hours. (3) One visit having two Discharge Diagnoses, one being "Bronchitis Asthmatic" and the other being "Asthma Disturbing Sleep." The encounter is of the type "outpatient" indicating that the patient stayed at the treatment facility for less than twenty-four hours. (4) One encounter having a Billing Diagnosis of "Asthma Disturbing Sleep." The encounter is of the type "outpatient" indicating that the patient stayed at the treatment facility for less than twenty-four hours. (5) One encounter having associated diagnoses.

Contemplate further that the patient data describing the above encounters is obtained and a query is performed to determine which encounters have occurred over a given time period (e.g., twelve months). Contemplate that all five encounters were within the subject time period. Data associated with each of the five encounters is examined and a "most significant diagnosis" is extracted for each. In embodiments, the "most significant diagnosis" may be determined according to a pre-established priority. For example, and not by way of limitation, contemplate that the following priority is utilized: Priority 1: Diagnosis Type=Discharge; Priority 2: Diagnosis Type=Reason for Visit; Priority 3: Diagnosis Type=Admitting; Priority 4:Diagnosis Type=Working; Priority 5: Diagnosis Type=Billing; Priority 6: Diagnosis Type=Suggested Billing; Priority 7: Diagnosis Type=Post-Op; Priority 8: Diagnosis Type=Pre-Op; Priority 9: Diagnosis Type=Final; Priority 10: Diagnosis Type=HC_Other; Priority 11: Diagnosis Type=HC_Principal; and Priority 12: Diagnosis Type=HC_Referring. Further contemplate that if more than one diagnosis shares the same "highest" priority, all the "highest priority" diagnoses may be used upon grouping.

In this example, following the same order of encounters listed (1)-(5), above, the following "most significant diagnoses" are determined: (1) The most significant diagnosis is "Diabetes Mellitus Complicating Pregnancy, Childbirth, or the Puerperium" since a Discharge Diagnosis has a higher priority than an Admitting Diagnosis. (2) The most significant diagnosis is "Diabetes Mellitus Type 1 with Ketoacidosis" since a Reason for Visit Diagnosis has a higher priority than a Working Diagnosis. (3) Both diagnoses have the same priority so both "Bronchitis Asthmatic" and "Asthma Disturbing Sleep" are considered most significant diagnoses for the encounter. (4) Only one diagnosis is available so it will be considered most significant. (5) No diagnosis is available for this encounter.

Once the diagnoses have been prioritized, a NomenclatureID associated with each one of the diagnoses may be retrieved. NomenclatureIDs are the unique identifiers in the system for the nomenclature(s) used to back the codified diagnoses associated with the patient encounters. The NomenclatureIDs may be used as parameters to query the ontology or nomenclature system, for example, the Discern Ontology database (provided by Cerner Corporation), for concepts matching the NomenclatureIDs. In the described instance, the result of this step is a map containing key-value pairs that represent the NomenclatureID and the matching Discern Ontology concept, if available.

In aspects, diagnoses for each encounter are prioritized and an attempt is made to find a match for each "most significant" diagnosis, for instance, in the map containing concepts from the ontology or nomenclature system, e.g., the Discern Ontology mappings. In other words, groups of encounters are generated and the ontology or nomenclature concepts are utilized to assign a name to the encounter groupings. Each grouping contains only encounters for which one or more diagnoses are logically linked to the ontology or nomenclature concept used to name the grouping. The same encounter may appear in more than one grouping, if diagnoses with the same priority and related to different ontology or nomenclature concepts are specified. Diagnoses that do not have an ontology or nomenclature mapping may be assigned to a grouping named with the specific diagnosis description. Encounters having no associated diagnoses may appear under a non-descript encounter grouping named, for instance, "Other."

Applying this process to the present exemplary scenario, the result is: (1) "Diabetes Mellitus Complicating Pregnancy, Childbirth, or the Puerperium" matches into the encounter grouping named "Diabetes Mellitus Other." (2) "Diabetes Mellitus Type 1 with Ketoacidosis" matches into the encounter grouping named "Diabetes Mellitus Type 1." (3) "Bronchitis Asthmatic" and "Asthma Disturbing Sleep" both match into the same ontology or nomenclature concept named "Asthma." (4) "Asthma Disturbing Sleep" also matches into the ontology or nomenclature concept named "Asthma."

The result of processing the diagnoses then may be stored in a data structure. In embodiments, the data structure holds the relationships between encounters, the diagnoses and their ontology or nomenclature encounter grouping. For the present exemplary scenario: (1) "Diabetes Mellitus Other": Containing only a relationship to "Diabetes Mellitus Complicating Pregnancy, Childbirth, or the Puerperium" for Encounter 1. (2) "Diabetes Mellitus Type 1": Containing only a relationship to "Diabetes Mellitus Type 1 with Ketoacidosis" for Encounter 2. (3) "Asthma": Containing relationships to "Bronchitis Asthmatic" and "Asthma Disturbing Sleep" for both Encounters 3 and 4. (4) "Other": This is a generic encounter grouping, used to hold the information for encounters that don't have associated diagnoses. Grouping (4) contains Encounter 5.

The data structures then are serialized and sent as part of the reply to the front-end to render a User Interface (UI) having a visual representation of the information. In embodiments, the resulting UI is composed of four encounter grouping indicators. A first represents three encounters and is labeled "Asthma." In exemplary embodiments, this indicator may be slightly bigger than the other ones since it represents more encounters. A second grouping represents one encounter and is labeled "Diabetes Mellitus Type 1." A third grouping represents one encounter and is labeled "Diabetes Mellitus Other." A fourth grouping represents one encounter and is labeled "Other."

In embodiments, upon selection of an indicator, a representation of the encounters (and the associated data) that are represented by the selected indicator is presented (e.g., a table containing a list of encounters). When a particular portion of the representation is selected (e.g., a row of a table), a detail pane having additional information (e.g., encounter date, treatment facility location (which may include a map), treatment provider, diagnosis detail, and the like) may be presented. In aspects (some of which are more fully described below), the indicators may be presented utilizing different colors depending on the type (or types) of encounters associated therewith. For instance, an orange indicator may indicate that at least one of the encounters in the encounter grouping is of type "in-patient" indicating that the patient stayed at the facility for more than twenty-four hours. (In the present exemplary scenario, the grouping indicator labeled "Diabetes Mellitus Other" may be orange in color.) A gray indicator may indicate that the encounters included in the associated grouping do not specify a diagnosis. (In the present exemplary scenario, the grouping indicator labeled "Other" may be gray in color.) A blue indicator may indicate that at least one of the encounters in the encounter grouping is of the type "out-patient" indicating that the patient stayed in the treatment facility for less than twenty-four hours. In embodiments, this grouping may further contain encounters that are otherwise regarded as less severe than hospitalizations. (In the present exemplary scenario, the grouping indicators labeled "Diabetes Mellitus Type 1" and "Asthma" may be blue in color.)

Aspects hereof further contemplate that in addition to diagnoses codes (and/or in lieu of diagnoses codes as such codes are not always associated with a patient encounter), data included in other fields associated with an Electronic Health Record (EHR) may be utilized to arrive at encounter groupings. Such additional fields may include, by way of example and not limitation, a 'Reason for Visit' field and a 'Procedures' field. Still further aspects contemplate that natural language processing may be utilized for fields such as a 'Chief Complaint' field or an 'Impression and Plan' field, or to garner meaningful terms from a general text box when such terms may be useful in understanding and grouping encounters. Any and all such variations, and any combinations thereof, are contemplated to be within the scope of the present technology.

Indicators in accordance with aspects hereof may include any conceivable visually discernible characteristics to indicate a common attribute amongst the encounters included in an encounter grouping. Exemplary visually discernible characteristics that may be included in aspects hereof, as well as attributes that may be associated with such characteristics, are described below. The description below contemplates a circular indicator having one or more of the additional visual characteristics described. It will be understood and appreciated by those having ordinary skill in the art that indicators having shapes that are other than circular may be utilized in accordance with aspects hereof and that the description focused on circular indicators is merely for ease of description. It further will be understood and appreciated by those having ordinary skill in the art that the characteristics, attributes, and characteristic/attribute pairings described below are exemplary in nature and in number and are not meant to limit the scope of aspects hereof in any way.

Indicator Size: In accordance with aspects hereof, visual indicators of varying sizes may be presented. In one exemplary aspect, a greater number of encounters may be indicated by a large indicator than the number of encounters indicated by a relatively smaller indicator. In aspects where the visual indicator or indicators are circular, the size may be represented by the diameter of the indicator. Aspects hereof contemplate that the number of encounters during a particular time period may be limited by a particular encounter location or include encounters across all encounter locations at which a patient has been treated.

Aspects hereof further contemplate scaling the size of encounter-location-based indicators in accordance with the nature of the encounter location. For instance, for an encounter location that is a walk-in clinic, the vast majority of patients may only be treated once or twice. If the size of all indicators is based solely on the number of encounters, all indicators representing encounters at such a location would be small and, accordingly, would not visually convey much useful information. Similarly, it may be that for an encounter location that treats, e.g., cancer patients, the vast majority of patients may have dozens of visits and, accordingly, most indicators representing encounters at such a location would be large—again, not conveying much useful information. Scaling the size of encounter-location-based indicators such that they are sized based upon what is more typical of the encounter location permits the indicators visually to provide context to indicators that are outliers relative to the norm for the location.

Still further, aspects hereof contemplate indicator sizes that are directly correlated to a characteristic associated with the indicator size. For instance, in aspects where the size of an indicator is indicative of a number of encounters associated with an encounter grouping, indicators that are directly correlated to the quantity of encounters represented thereby may be utilized. In such aspects, an indicator representing a greater number of encounters will generally be larger than an indicator representing a lesser number of encounters. Additional aspects contemplate a finite and defined maximum number of potential indicator sizes (e.g., ten indicator sizes). In such aspects, encounter groupings having numbers of encounters falling within a quantity range may be represented by an indicator of the same size. For instance, an encounter grouping having eight encounters associated therewith and an encounter grouping having ten encounters associated therewith may be associated with an indicator having the same size. Any and all such variations, and any combination thereof, are contemplated to be within the scope of the present technology.

Indicator Color: In accordance with aspects hereof, visual indicators of different colors may be presented. In exemplary aspects, a first color indicator (e.g., an orange indicator) may be representative of inpatient encounters (in which the patient stays more than twenty-four hours) or hospitalizations and a second color indicator (e.g., a blue indicator) may be representative of outpatient encounters (in which the patient stays less than twenty-four hours). In other exemplary aspects, a first color indicator (e.g., an orange indicator) may be representative of encounters regarded as more severe (for instance, hospitalizations and surgeries—whether inpatient or outpatient) and a second color indicator (e.g., a blue indicator) may be representative of encounters that are regarded as less severe (e.g., outpatient encounters excepting surgeries, clinical trials, etc.). In additional aspects, a particular color indicator may provide insight not only into the severity of a condition for which an encounter has occurred but convey specific information about the nature of the encounter. For instance, a particular color indicator (e.g., a purple indicator) may be indicative of a radiation treatment encounter.

Further aspects hereof contemplate a visual indicator having a third color (e.g., green) that is representative of a patient-defined priority. For instance, a patient may be being actively treated for multiple conditions (e.g., anemia and hypertension). The patient may be treated more regularly (and thus, more often) for the hypertension than the anemia and, accordingly, the indicator associated with encounters related to the hypertension diagnosis may be larger than the indicator associated with an anemia diagnosis. It is additionally likely that all the encounters associated with both the anemia and the hypertension diagnoses are outpatient and/or considered less severe than a surgery or hospitalization and, accordingly, these indicators may be of the same color. However, the patient may feel that his or her hypertension is well-controlled but that he or she needs additional help controlling the anemia. Aspects permitting the patient to designate a patient-defined priority thus allow a readily discernible indication of the patient's concern that would not otherwise be conveyed by an indicator for anemia having a relatively smaller size and same color as an indicator for hypertension.

Aspects hereof contemplate that a treatment provider may set a patient priority (for instance, by selection of a 'Patient Priority' check-box associated with documentation of a patient encounter) or that a patient (for instance, through a portal permitting viewing and editing of one or more portions of a patient's EHR data) may set his or her priority (e.g., by selection of a check-box or the like). Any and all such variations, and any combination thereof, are contemplated to be within the scope of the present technology.

Indicator Halos: Aspects hereof contemplate indicators having a perimeter "halo" characteristic. A "halo" as the term is utilized herein, refers to a visually discernible attribute of an indicator that generally extends around at least a portion of the perimeter of an indicator and permits maintenance of the other visual characteristics of the indicator (e.g., shape, relative size and color), but that imparts additional information that may be readily ascertained by a viewer. In one exemplary aspect, a perimeter halo extends around the entire perimeter of an indicator with the width thereof being correlated to the relevant attribute of the associated encounter grouping. By way of example, in exemplary aspects, a perimeter halo may indicate an encounter grouping for a diagnosis for which the subject patient has been treated at multiple encounter locations. In a more specific exemplary aspect, the width of such a halo may be correlated to the number of encounter locations associated with the represented encounter grouping; encounter groupings having a greater quantity of encounter locations having a halo with a greater width measurement than encounter groupings having a lesser relative quantity of encounter locations associated therewith.

Further aspects hereof contemplate halos having a measurement (e.g., a width measurement) that arise directly correlated to a characteristic associated therewith. For instance, in aspects where a halo is representative of multiple encounter locations included within the encounters associated with an encounter grouping, the measurement (e.g., the width) of the halo may be directly representative of the quantity of encounter locations represented thereby. In such aspects, a halo representing a greater number of encounter locations may be larger than a halo representing a lesser number of encounter locations. Additional aspects contemplate a finite and defined maximum number of potential halo measurements (e.g., five width sizes). In such aspects, a halo representing, for instance, a number of encounter locations falling within a quantity range may be represented by a halo of the same size. For instance, an encounter grouping having three encounter locations associated therewith and an encounter grouping having four encounter locations associated therewith may be associated with a halo having the same measurement (e.g., width). Any and all such variations, and any combination thereof, are contemplated to be within the scope of the present technology.

Accordingly, embodiments of the present invention relate to one or more computer storage media storing computer-useable instructions that, when used by one or more computing devices, cause the one or more computing devices to perform a method for visualizing patient conditions over time. The method comprises: identifying a plurality of encounters associated with a particular patient; organizing the plurality of encounters into one or more encounter groupings, encounters of the plurality of encounters that are grouped into a particular encounter grouping sharing at least one similar characteristic; and presenting an encounter indicator for each of the one or more encounter groupings, the encounter indicator representing the encounters that are grouped into the particular encounter grouping, each encounter indicator having at least one visual characteristic that conveys information about the encounters that are represented thereby.

Embodiments of the present invention further relate to a method for visualizing patient conditions over time. The method comprises: identifying a plurality of encounters associated with a particular patient, each of the plurality of encounters sharing at least one similar characteristic; organizing the plurality of encounters into an encounter grouping; and presenting an encounter indicator for the encounter grouping, the encounter indicator having at least one visual characteristic that conveys information about the plurality of encounters that is represented thereby.

Still further, embodiments of the present invention relate to one or more computer storage media storing computer-useable instructions that, when used by one or more computing devices, cause the one or more computing devices to perform a method for visualizing patient conditions over time. The method comprises: identifying a plurality of encounters associated with a particular patient, each of the plurality of encounters occurring in a particular timeframe; organizing the plurality of encounters into a plurality of encounter groupings, wherein encounters that are organized in the same encounter grouping share a similar diagnosis;

presenting an encounter indicator for each of the plurality of encounter groupings, the encounter indicator representing the encounters that are organized in the same encounter grouping, each encounter indicator having at least one visual characteristic that conveys information about the encounters that are represented thereby; and presenting a timeline, the timeline having a temporal indicator for each of the plurality of encounters, the temporal indicators illustrating a relative time in which each of the plurality of encounters occurred.

Figure 1:
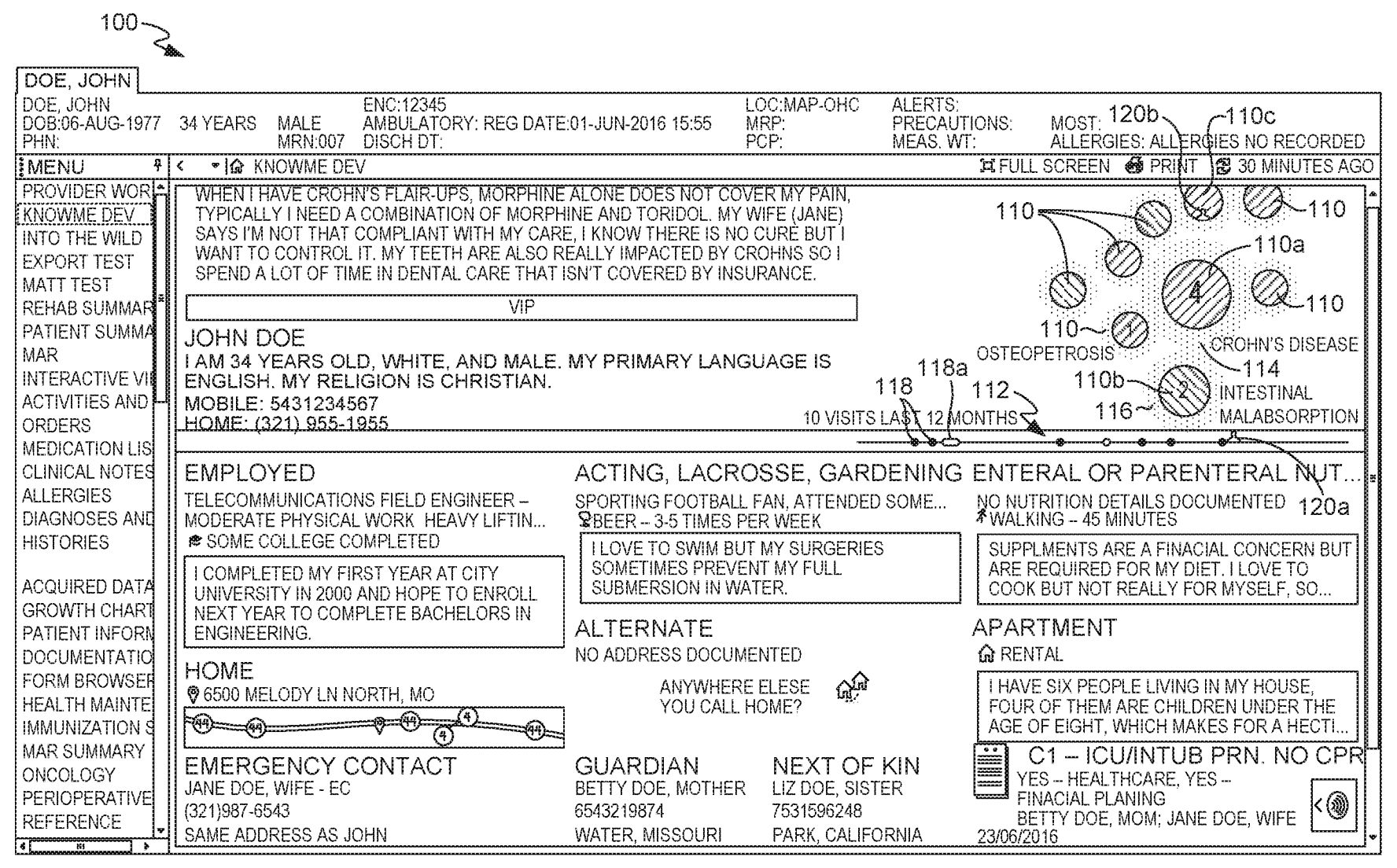

Turning now to FIG. 1, depicted is an exemplary screen display 100 having a plurality of encounter indicators 110 each representing a group of encounters for a patient by the name of "John Doe" over the course of ten encounters occurring over the previous twelve-month time frame (the timeline being indicated by reference numeral 112). Each encounter indicator 110 represents an encounter grouping and includes visually discernible characteristics that are indicative of an attribute common amongst the encounters included in the encounter grouping. For instance, as illustrated by diagonal lines extending in a downward direction from right to left, indicator 110a may be blue in color (in this instance indicating a non-severe, outpatient encounter grouping), the largest in size of all indicators 110 (in this instance indicating the encounter grouping represented thereby includes the largest number of patient encounters over the previous twelve month time frame relative to all other represented encounter groupings), and includes a perimeter halo 114 (in this instance indicating that the patient encounters included in the represented encounter grouping took place at multiple treatment locations). The perimeter halo 114 is larger than any other illustrated perimeter halos, in this instance indicating that the represented encounter grouping includes the relatively largest number of patient encounter locations. The illustrated encounter indicator also includes the numeral "4" in the center thereof indicating the quantity of encounters represented in the encounter grouping.

As illustrated by diagonal lines extending in a downward direction from left to right, another encounter indicator 110b may be orange in color. In this instance, such indicates that the encounters included in the encounter grouping are hospitalizations and/or relatively severe outpatient encounters (e.g., surgeries). The encounter indicator 110b is smaller in size than encounter indicator 110a (in this instance indicating the encounter grouping represented includes fewer encounters than the encounter grouping represented by encounter indicator 110a). The encounter indicator 110b also includes the numeral "2" in the center thereof indicating the quantity of encounters represented by the encounter grouping. While in comparing only encounter indicators 110a and 110b, the size of the indicator may seem irrelevant given the fact that the quantity of encounters is explicitly represented as a numerical quantity. However, the size of the encounter indicators remains a quick indication of the quantity of encounters represented; particularly relative to those encounter indicators representing encounter groupings for which there is no quantity visually depicted in association therewith.

Also associated with encounter indicator 110b is a perimeter halo 116 (in this instance indicating that the patient encounters included in the represented encounter grouping took place at multiple treatment locations). The perimeter halo 116 is smaller (i.e., has a lesser width) than perimeter halo 114, in this instance indicating that the represented encounter grouping includes relatively fewer patient treatment locations.

Encounter indicator 110a additionally includes a title ("Crohn's Disease") representing a common attribute among the encounters included in the represented encounter grouping. In this instance, the title is representative of a high-level diagnosis associated with each encounter included in the encounter grouping. Similarly, indicator 110b includes a title "Intestinal Malabsorption," indicating that each encounter included in the represented encounter grouping is associated with such high-level diagnosis.

The timeline 112 includes temporal indicators 118—one for each encounter that is represented in the encounter groupings associated with the encounter indicators 110. The temporal indicators 118 include at least one visual characteristic that is similar to the encounter indicators 110. In this instance, though difficult to discern in the black-and-white figure, the temporal indicators 118 may be of the same color as the encounter indicators 110 represented thereby. For instance, the temporal indicators may be blue to represent outpatient, non-severe encounters and orange to represent hospitalization or outpatient surgery encounters in embodiments where the encounter indicators 110 are similarly colored. Additionally, the temporal indicators 118 are shown at a location on the timeline that indicates when in the timeline the represented encounter occurred. Still further, the temporal indicators 118 are of a size that indicates the length of the encounter. For instance, temporal indicator 118a is laterally elongated relative to the other temporal indicators, indicating that it represents a hospital stay of more than twenty-four hours whereas the other temporal indicators represent stays at treatment facilities of less than twenty-four hours. In aspects hereof, hovering over (or otherwise selecting) a temporal indicator results in the presentation of some detail giving insight into the encounter represented thereby.

An icon of a figure head is illustrated both on the timeline 120a and in association with one of the encounter indicators 120b. As illustrated, such figure head icon 120a associated with the timeline 112 visually indicates the visit for which the viewer (likely a treatment provider) was last involved with an encounter with the patient. The figure head icon 120b illustrated in association with the encounter grouping indicator 110c indicates the encounter grouping with which the viewer's last encounter with the patient is associated.

Figure 2:
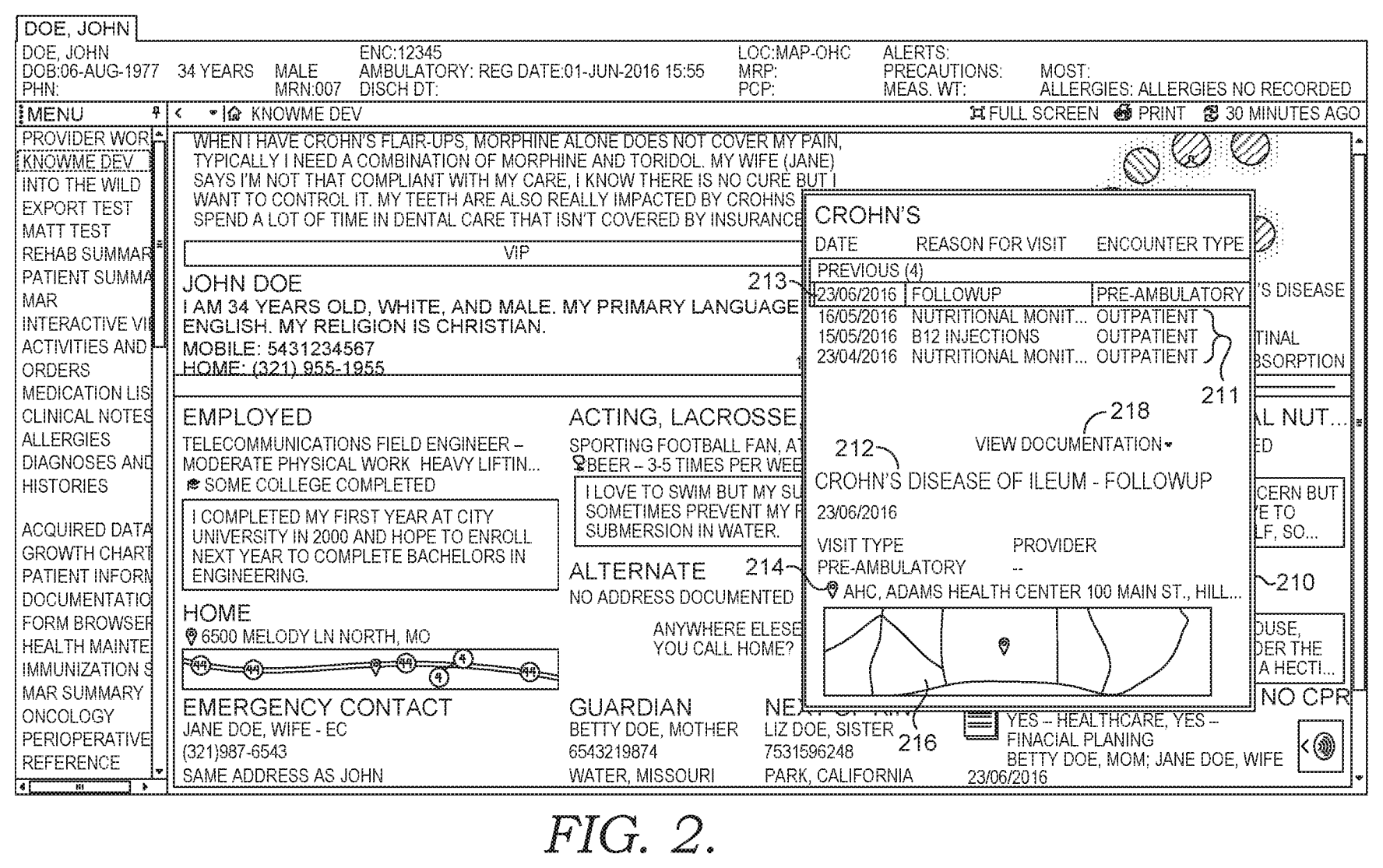

In aspects hereof, hovering over (or otherwise selecting) an encounter grouping indicator 110 results in the presentation of some detail regarding the encounters included in the relevant grouping. For instance, with reference to FIG. 2, it can be seen that hovering over the encounter grouping indicator 110a (FIG. 1) causes presentation of a window 210 showing a listing 211 of limited information regarding the four encounters included in the grouping. As illustrated, the first of such encounters 213 is highlighted/selected and more detailed information 212 regarding the selected encounter 213 is presented beneath the listing 211. It can be seen that the listing 211 shows only a date associated with the encounter 213 (23 Jun. 2016) and a reason for the encounter 213 of "followup." The more detailed information 212 shows that the followup visit was for "Crohn's disease of ileum" and also shows an identifier 214 of a treatment location associated with the encounter, including a portion of a map 216 showing the treatment location. Visualizing the treatment location in this way permits planning of future encounters based on proximity to one another to alleviate inconvenience to the patient.

Figure 3:
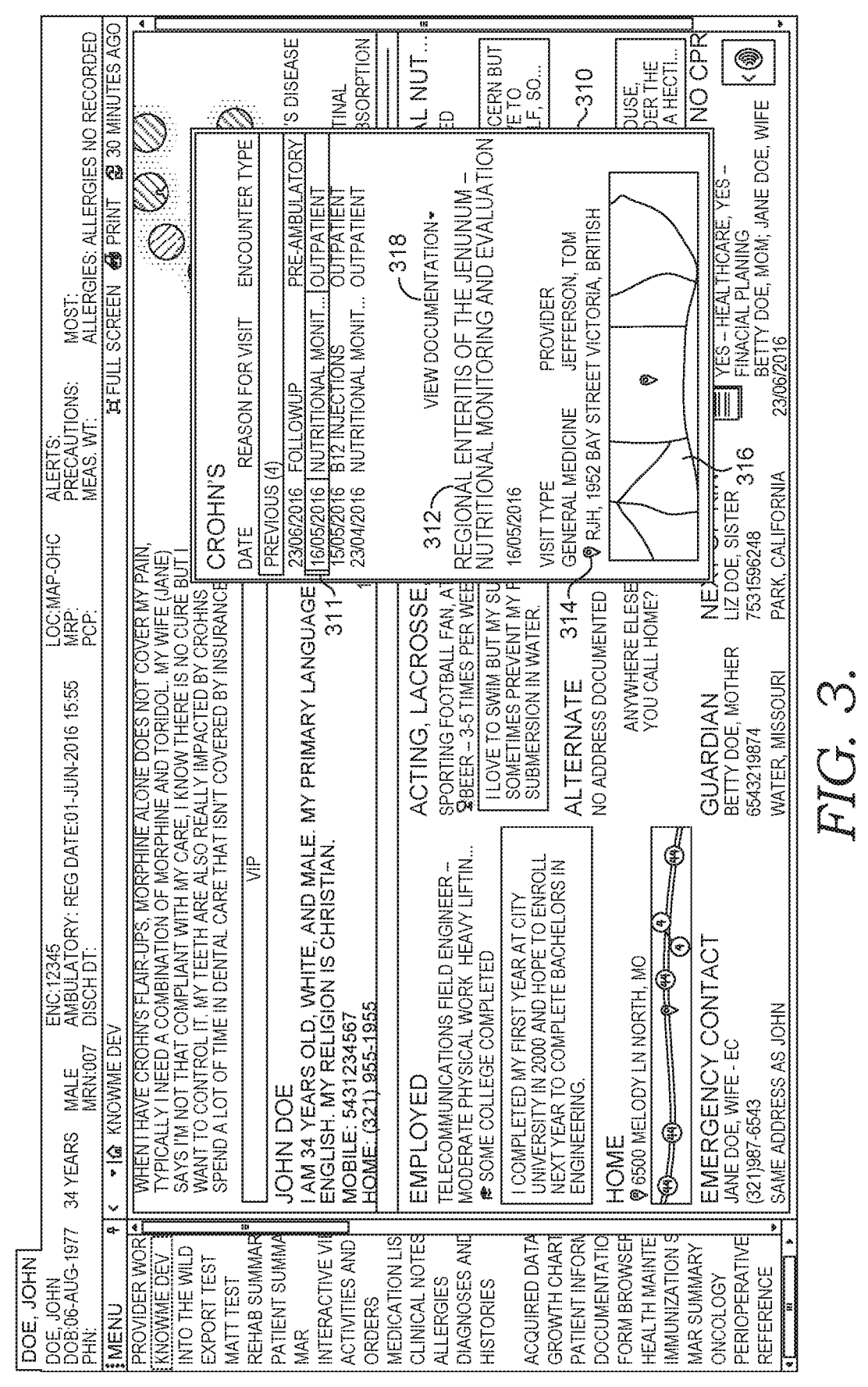

With reference to FIG. 3, the second listed encounter 311 included in the encounter grouping represented by indicator 110 a (FIG. 1) causes presentation of a window 310 showing more detailed information 312 regarding the represented encounter 311 is presented beneath the listing. It can be seen that the listing shows only a date associated with the encounter 312 (16 May 2016) and a reason for the encounter of "nutritional monit . . . " The more detailed information 312 shows that the encounter was a "nutritional and monitoring visit" and, more specifically, was for "Regional enteritis of the jejunum." The more detailed information 312 also shows an identifier 314 of a treatment location associated with the encounter 312, including a portion of a map 316 showing the location.

Figure 4:
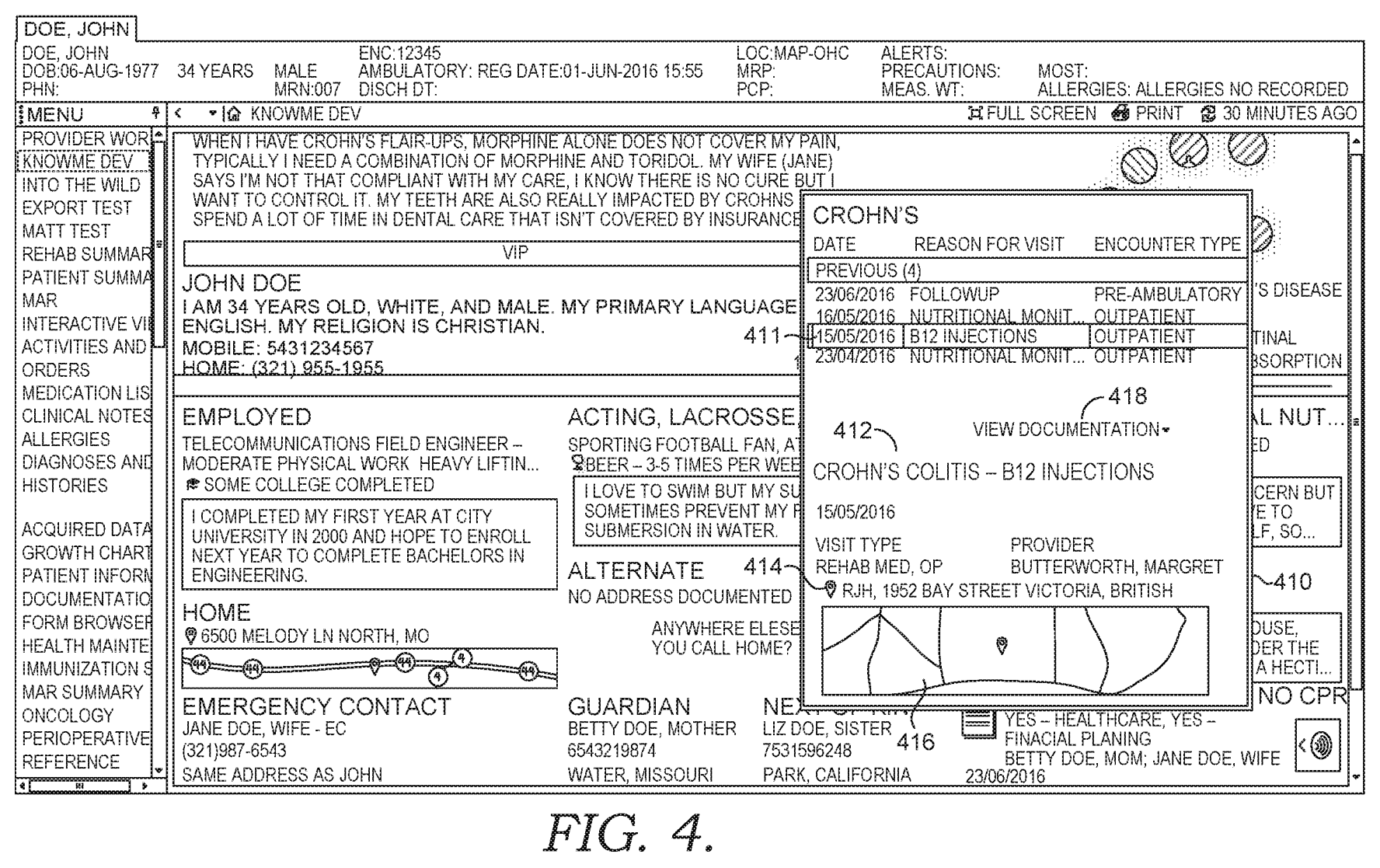

With reference to FIG. 4, the third listed encounter 411 included in the encounter grouping represented by indicator 110 *a* (FIG. 1) causes presentation of a window 410 showing more detailed information 412 regarding the represented encounter is presented beneath the listing. It can be seen that the listing shows only a date associated with the encounter 411 (15 May 2016) and a reason for the visit of "B12 injections." The more detailed information 412 shows that the B12 injections were for "Crohn's colitis" and also shows an identifier 414 of a treatment location associated with the encounter 411, including a portion of a map 416 showing the location.

Figure 5:
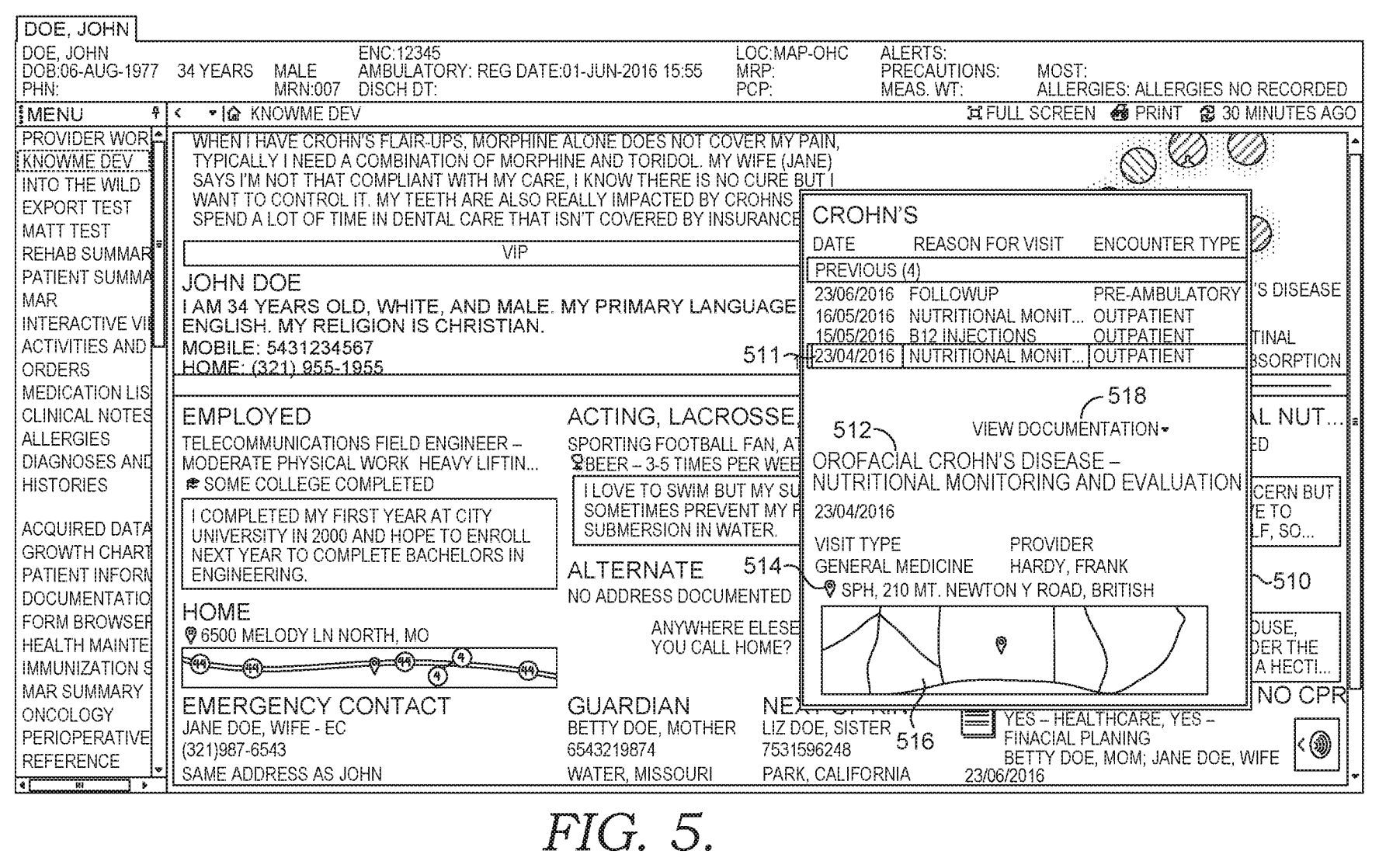

With reference to FIG. 5, the fourth listed encounter 511 included in the encounter grouping represented by indicator 110 *a* (FIG. 1) causes presentation of a window 510 showing more detailed information 512 regarding the represented encounter is presented beneath the listing. It can be seen that the listing shows only a date associated with the encounter 511 (23 Apr. 2016) and a reason for the visit of "nutritional monit . . . " The more detailed information 512 shows that the encounter was for "nutritional monitoring and evaluation" and, more particularly, was for "Orofacial Crohn's disease." The more detailed information 512 also shows an identifier 514 of a treatment location associated with the encounter 511, including a portion of a map 516 showing the location.

In each of the encounters included in the encounter grouping represented by indicator 110*a,* the more detailed information indicates something different: "Crohn's disease of ileum—followup" (first listed encounter), "Regional enteritis of the jejunum—nutritional monitoring and evaluation" (second listed encounter), "Crohn's colitis—B12 injections" (third listed encounter), and "Orofacial Crohn's disease—nutritional monitoring and evaluation" (fourth listed encounter). However, as each of these encounters is included in a single encounter grouping, represented by the title "Crohn's disease," it is evident that each encounter is associated with that more general diagnosis.

In FIGS. 2-5, a selection box (218, 318, 418, and 518 respectively) indicating "View Documentation" is shown. Selection of the selection box permits more detailed documentation of the associated visit to be presented. In this way, more complete documentation associated with an encounter may be quickly and easily viewed without the user having to navigate to other areas of the associated EHR.

Turning now to FIG. 6, an additional exemplary view of encounter-driven grouping indicators is shown. As illustrated, each encounter indicator 610 is representative of a single encounter and the indicators are grouped into temporal clusters—a timeline 612 related to the data being shown. A couple of features are to be noted from FIG. 6. The first is a body map 614. The body map 614 shows where on the patient's body diagnoses related to a given encounter are found. For instance, some encounters represented in FIG. 6 relate to the patient's heart, some encounters relate to the patient's abdominal region, some encounters relate to the patient's head region, and some encounters relate to the patient's ankle region. In embodiments, the indicators appearing on the body map may be presented with a visual characteristic (e.g., a color) that corresponds to a color of the encounter indicators representing encounters related to the subject body region. For instance, some encounter indicators 610 may be green, while others may be orange or purple. Additionally, the indicator on the body map 614 related to the heart may be green, the indicator on the body map 614 related to the abdominal region may be orange, and the indicator on the body map 614 related to the head region may be purple. In this instance, the encounter indicators 610 that are green represent encounters where the patient was seen in relation to the heart, the orange encounter indicators 610 represent encounters where the patient was seen in relation to the abdominal region and the encounter indicators 610 that are purple represent encounters where the patient was seen in relation to the head region. It will be understood that the colors and corresponding body map regions are described herein by way of example only and not limitation. Any color, or any other visually discernible characteristic, may be utilized within the scope of embodiments hereof.

The second noteworthy feature of FIG. 6 is the trend line 616. The trend line 616 permits a patient's encounters over time to be viewed as a whole and readily illustrates when (in time) a patient was at their healthiest, when they were under the most intensive care and for which conditions, when a particular condition was particularly problematic, etc. Such trend line 616 provides a quick generalization of a patient's health over time.

The third noteworthy feature of FIG. 6 is the timeline 618. The timeline 618 includes a selectable and moveable indicator 620 associated therewith. Changing the position of the indicator 620 along the timeline 618 may result in a change in the view represented. That is, one or more of the temporal indicator clusters, the trendline 616 and the body map 614 may be altered based upon the state of the patient at the time on the timeline 618 where the moveable indicator 620 presently resides. For instance, as shown in FIG. 6, the view represents the condition of the patient in 2015 as this is where the moveable indicator 620 resides. Moving the indicator 620 to the left would permit a view into the patient's condition(s) at other past times, even as early as 2005, likely altering the presentation of most, if not all, of the information shown.

Figure 7:
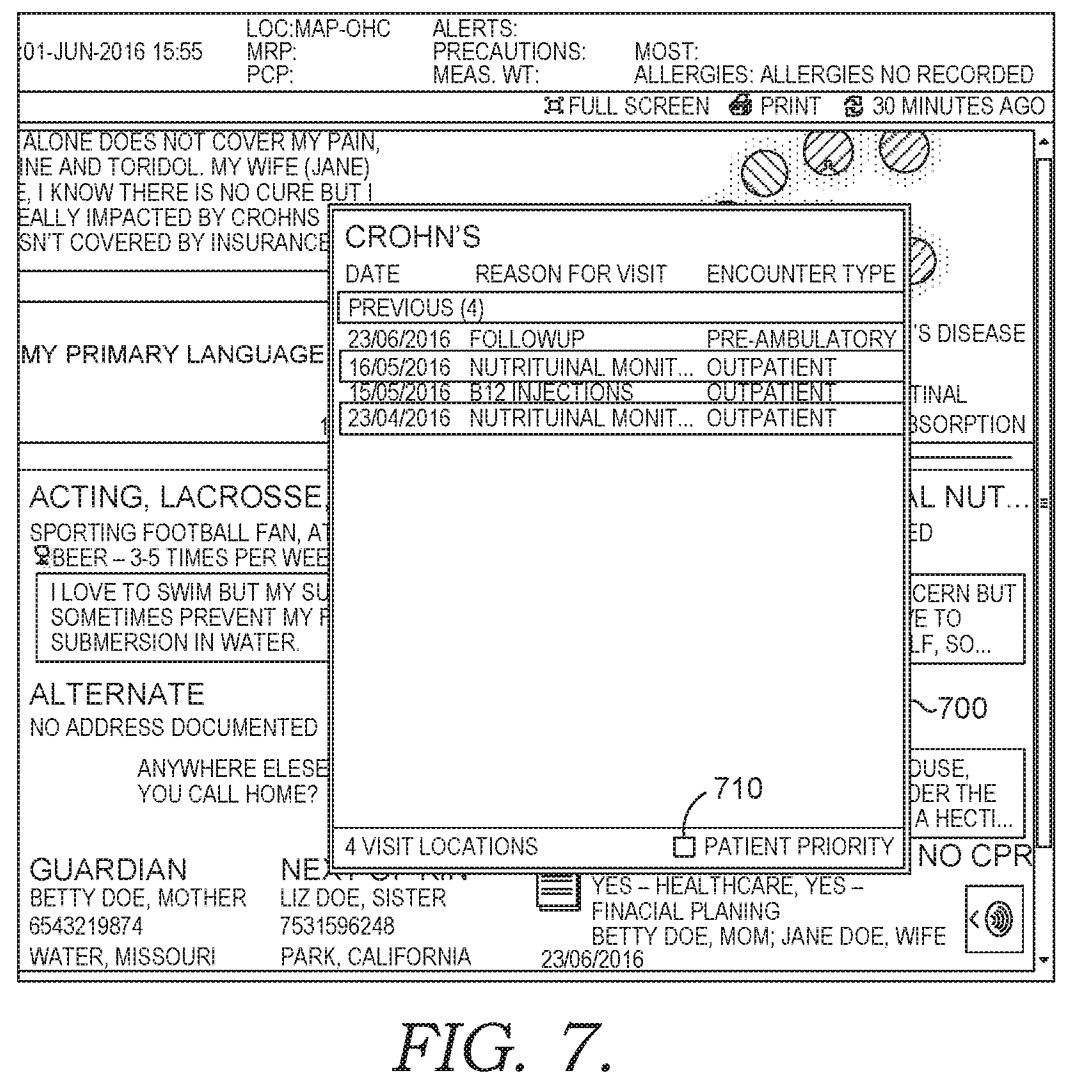
Figure 8:
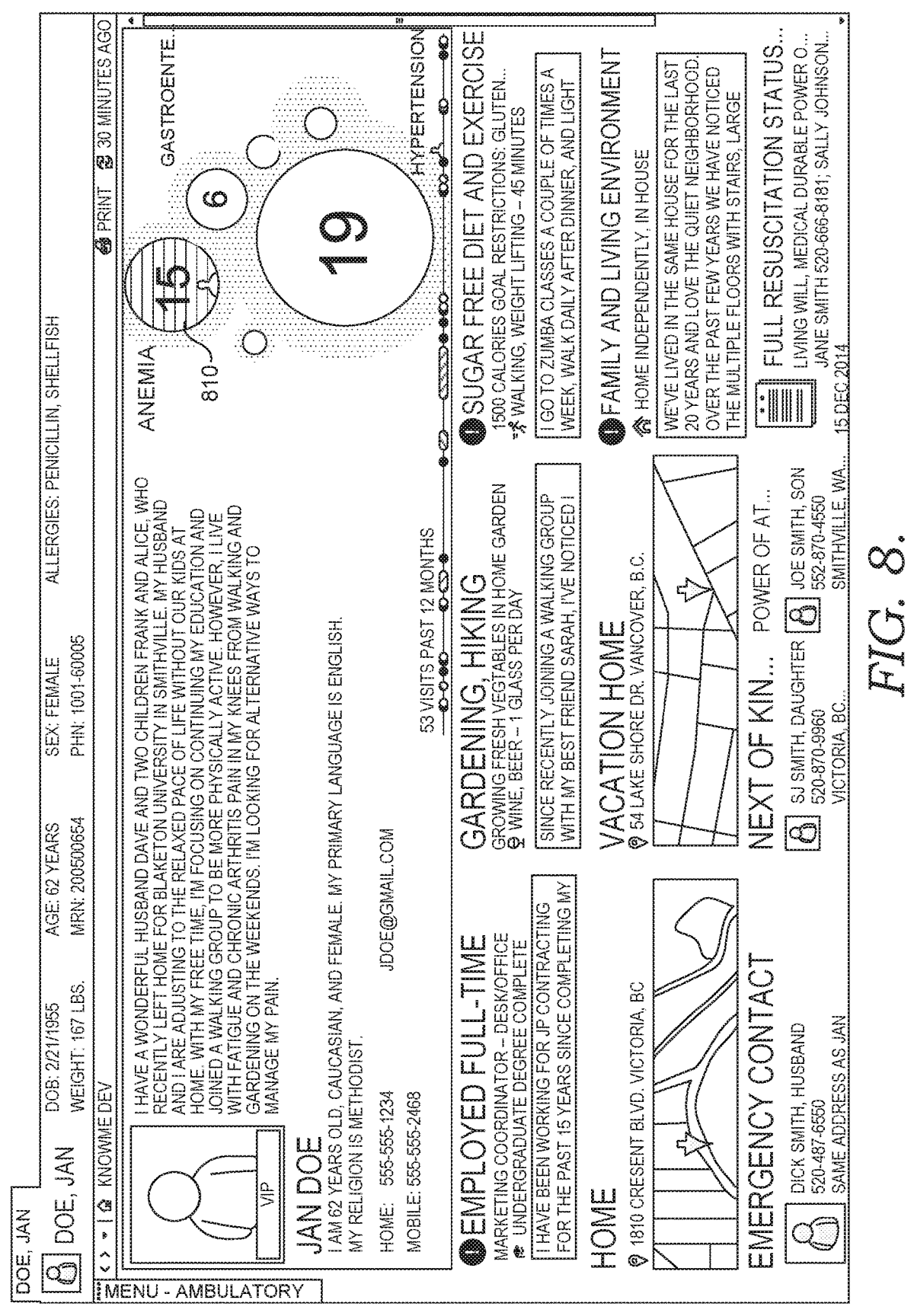

As previously set forth, aspects hereof contemplate that a patient (or a treatment provider) may select a priority for one or more conditions for which the patient is particularly concerned. FIG. 7 illustrates a selection box 710 that permits the setting of such priority. In accordance with aspects hereof, hovering over (or otherwise selecting, e.g., right-clicking) a particular indicator (in this case indicator 110*a* (FIG. 1)) may result in presentation of a window 700 listing the encounters associated with the encounter grouping represented by the indicator and a "Patient Priority" check box. Selection of the check box 710 may result, in this instance, in the indicator having a changed visual characteristic relative to other encounter indicators to indicate the patient-driven priority. By way of example, the color of the subject encounter indicator may be changed to a color reserved only for patient priority indicators. This is indicated with reference to FIG. 8 wherein the encounter indicator 810 has a distinct visual appearance not shared by any other encounter indicators, indicating that the encounter grouping includes encounters for which the patient is particularly concerned.

Figure 9:
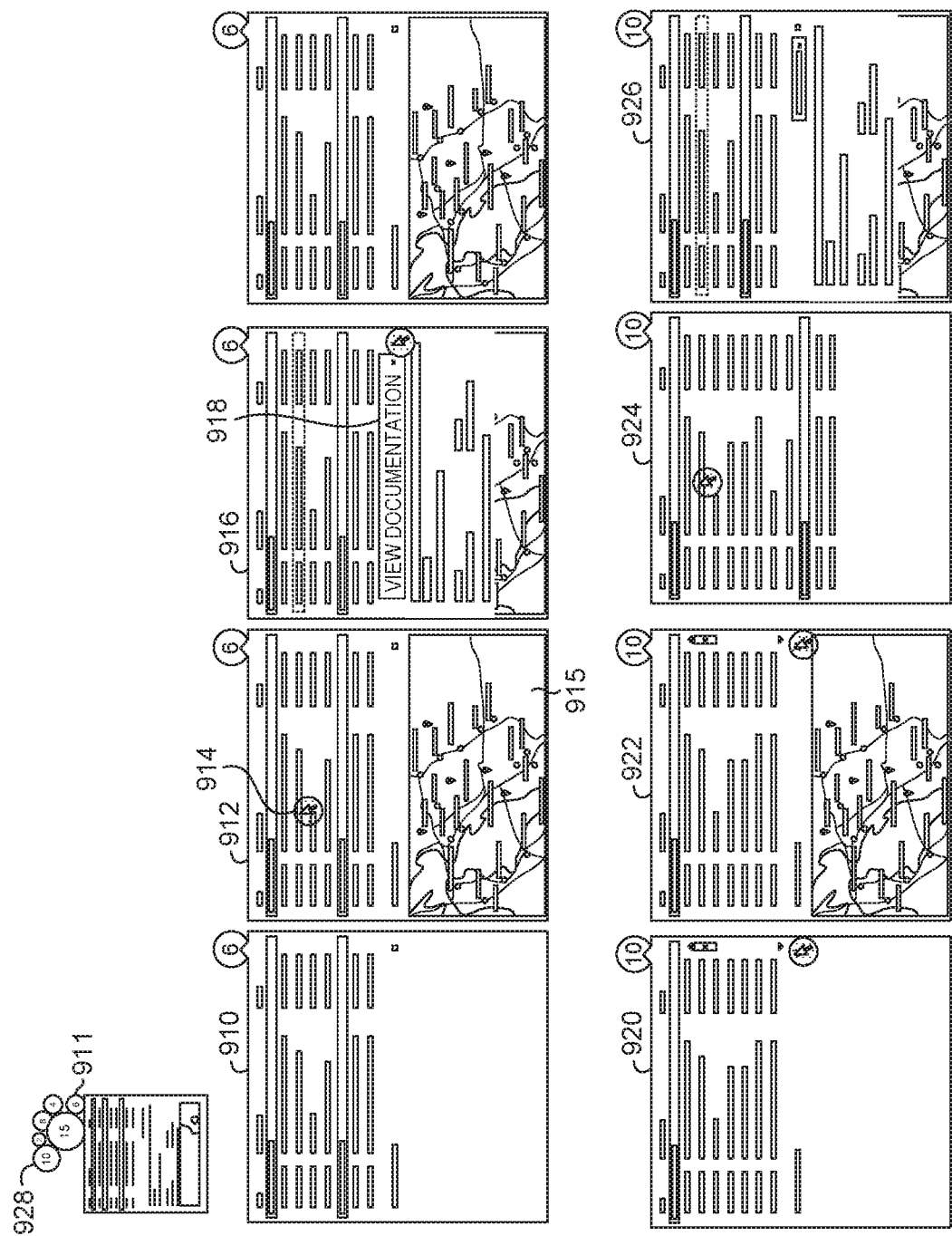
FIG. 9 depicts exemplary screen displays illustrating encounter information, in accordance with aspects hereof.

FIG. 9 illustrates further examples of encounter selection associated with an encounter grouping indicator, and how hovering over (or otherwise selecting) a particular listed encounter can result in display of map information related to an encounter location. Window 910 illustrates an exemplary encounter listing. The encounter listing corresponds to the encounter indicator 911 having six encounters associated therewith. Window 912 illustrates the encounter listing of window 910 with a selection indicator 914 hovering over the second encounter in the listing. Window 912 further illustrates a map 915 of the various encounter locations. Window 916 illustrates some additional information with respect to the encounter selected in window 912 (similar to the view of FIGS. 2-5). FIG. 9 further illustrates a "view documentation" selection box 918, selection of which permits viewing of documentation supporting the encounter and listing information. Similar window views are illustrated in windows 920, 922, 924, and 926, with the information contained therein being related to the encounter indicator 928 having ten encounters associated therewith.

Figure 10:
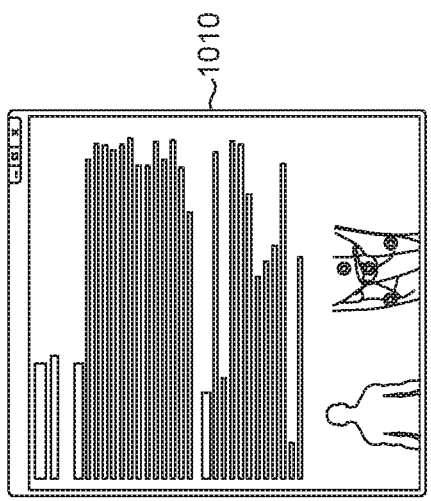
FIG. 10 depicts exemplary screen displays illustrating documentation and mapping information associated with an encounter, in accordance with aspects hereof.
Figure 10:
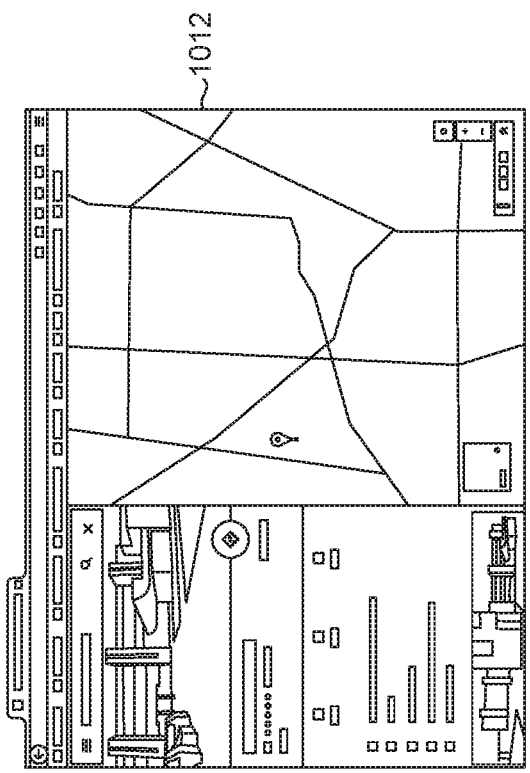
Figure 10:
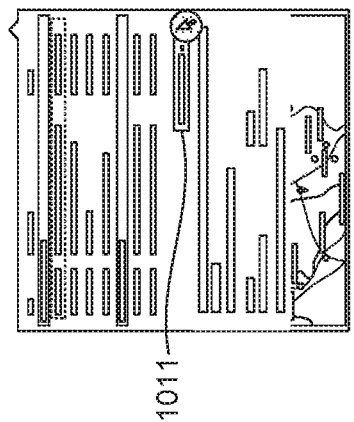
Figure 10:
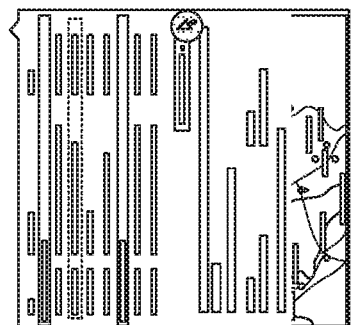

FIG. 10 illustrates a window 1010 into additional documentation that may be associated with selection of a "view documentation" selection box 1011, and an expanded view 1012 of map data that may be viewed upon selection of a map indicator associated with an encounter location.

Figure 11:
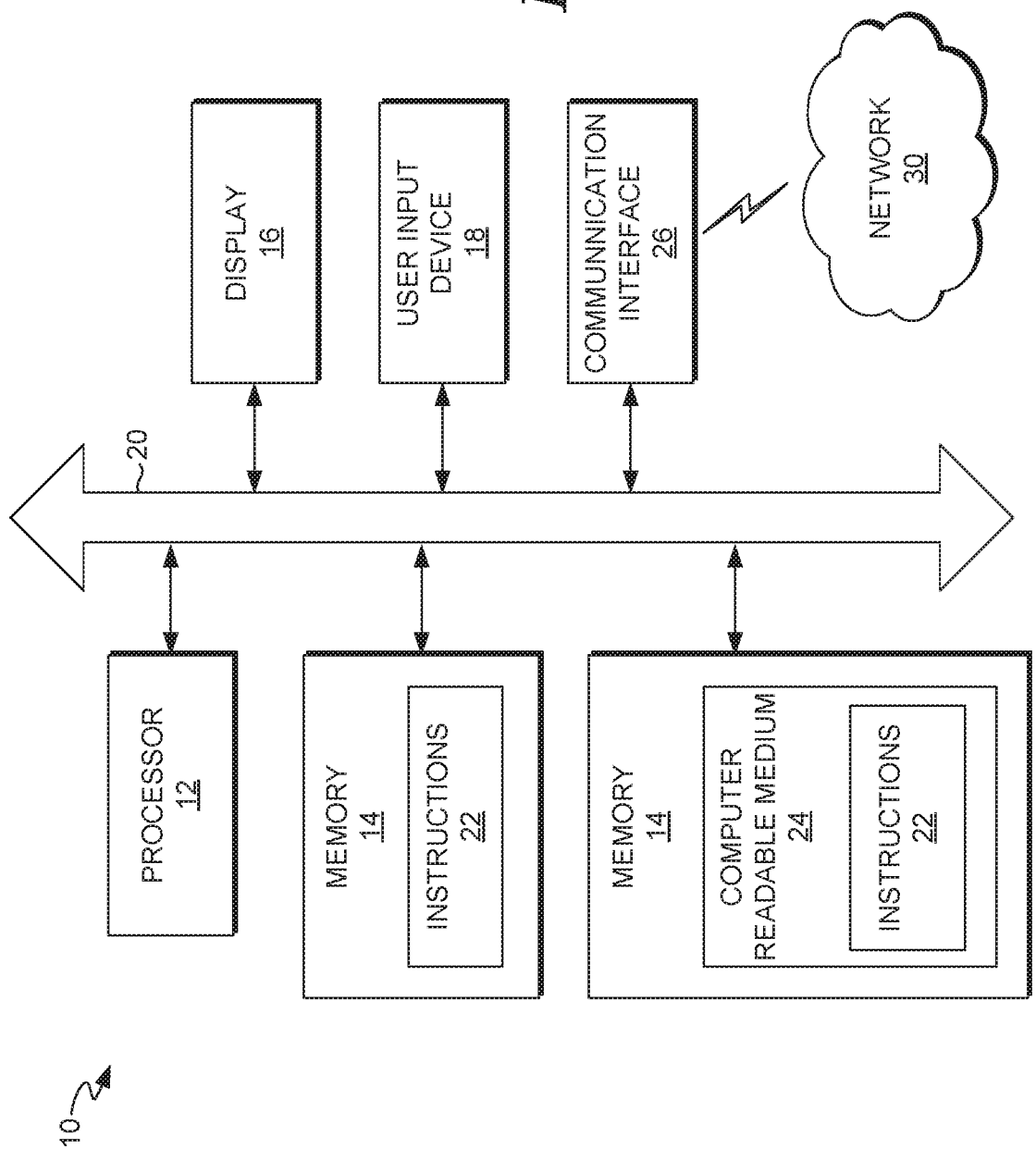
FIG. 11 depicts an illustrative computer system for visualizing patient encounters, in accordance with aspects hereof.

FIG. 11 provides an illustrative embodiment of a general computer system 10 for visualizing patient encounter in accordance with aspects of the present technology. The computer system 10 can include a set of instructions that can be executed to cause the computer system 10 to perform any one or more of the methods or computer based functions disclosed herein. The computer system 10 may operate as a standalone device or may be connected, e.g., using a network, to other computer systems or peripheral devices. Any of the embodiments discussed above may be implemented using the computer system 10, multiple computer systems 10, or a component in the computer system 10.

In a networked deployment, the computer system 10 may operate in the capacity of a server or as a client user computer in a client-server user network environment, or as a peer computer system in a peer-to-peer (or distributed) network environment. The computer system 10 can also be implemented as or incorporated into various devices, such as a personal computer (PC), a tablet PC, a set-top box (STB), a personal digital assistant (PDA), a mobile device, a palmtop computer, a laptop computer, a desktop computer, a communications device, a wireless telephone, a land-line telephone, a control system, a camera, a scanner, a facsimile machine, a printer, a pager, a personal trusted device, a web appliance, a wearable medical device, a network router, switch or bridge, or any other machine capable of executing a set of instructions (sequential or otherwise) that specify actions to be taken by that machine. In a particular embodiment, the computer system 10 can be implemented using electronic devices that provide voice, video or data communication. Further, while a single computer system 10 is illustrated, the term "system" shall also be taken to include any collection of systems or sub-systems that individually or jointly execute a set, or multiple sets, of instructions to perform one or more computer functions.

As illustrated in FIG. 11, the computer system 10 may include a processor 12, e.g., a central processing unit (CPU), a graphics processing unit (GPU), or both. The processor 12 may be a component in a variety of systems. For example, the processor 12 may be part of a standard personal computer or a workstation. The processor 12 may be one or more general processors, digital signal processors, application specific integrated circuits, field programmable gate arrays, servers, networks, digital circuits, analog circuits, combinations thereof, or other now known or later developed devices for analyzing and processing data. The processor 12 may implement a software program, such as code generated manually (i.e., programmed).

In an embodiment, the processor 12 may be configured to cause the system 10 to identify data indicative of an event relating to the medication, the event involving a change related to the medication, determine at least one task for a course of care of at least one patient due to the change related to the medication, select, by accessing the treatment provider repository, at least one treatment provider for the at least one patient, the treatment provider selected from a plurality of treatment providers having associated provider attributes, and the selecting being based on the change related to the medication, the provider attributes, and at least one patient characteristic from a patient medical record database, and provide to the selected at least one treatment provider a notification that indicates the event, the identified at least one patient, and that the selected treatment provider is a designated treatment provider for the at least one task.

The computer system 10 may include a memory 14 that can communicate via a bus 20. The memory 14 may be a main memory, a static memory, or a dynamic memory. The memory 14 may include, but is not limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one embodiment, the memory 14 includes a cache or random access memory for the processor 12. In alternative embodiments, the memory 14 is separate from the processor 12, such as a cache memory of a processor, the system memory, or other memory. The memory 14 may be an external storage device or database for storing data. Examples include a hard drive, compact disc ("CD"), digital versatile disc ("DVD"), memory card, memory stick, floppy disc, universal serial bus ("USB") memory device, or any other device operative to store data. The memory 14 is operable to store instructions executable by the processor 12. The functions, acts or tasks illustrated in the figures or described herein may be performed by the programmed processor 12 executing the instructions 22 stored in the memory 14. The functions, acts or tasks are independent of the particular type of instructions set, storage media, processor or processing strategy and may be performed by software, hardware, integrated circuits, firm-ware, micro-code and the like, operating alone or in combination Likewise, processing strategies may include multiprocessing, multitasking, parallel processing and the like.

In an embodiment, the memory 14 and/or computer readable medium 24 may be operable to store a database comprising a treatment provider repository having a plurality of treatment providers, the plurality of treatment providers associated with provider attributes, and an electronic patient medical record database.

As shown, the computer system 10 may further include a display unit 16, such as a liquid crystal display (LCD), an organic light emitting diode (OLED), a flat panel display, a solid state display, a cathode ray tube (CRT), a projector, a printer or other now known or later developed display device for outputting determined information. The display 16 may act as an interface for the user to see the functioning of the processor 12, or specifically as an interface with the software stored in the memory 14 or in the drive unit 25. The display 16 may be operable to present notifications containing information regarding a medical course of care.

Additionally, the computer system 10 may include an input device 18 configured to allow a user to interact with any of the components of system 10. The input device 18 may be a number pad, a keyboard, or a cursor control device, such as a mouse, or a joystick, touch screen display, remote control or any other device operative to interact with the system 10. The input device 18 may be configured to receive information from a user regarding a medical course of care.

In a particular embodiment, as depicted in FIG. 11, the computer system 10 may also include a disk or optical drive unit 25. The disk drive unit 25 may include a computer-readable medium 24 in which one or more sets of instructions 22, e.g. software, can be embedded. Further, the instructions 22 may embody one or more of the methods or logic as described herein. In a particular embodiment, the instructions 22 may reside completely, or at least partially, within the memory 14 and/or within the processor 12 during execution by the computer system 10. The memory 14 and the processor 12 also may include computer-readable media as discussed above.

As is also indicated above, in an embodiment, the memory 12 and/or the computer readable medium 24 may be operable to store a database comprising a treatment provider repository having a plurality of treatment providers, the plurality of treatment providers associated with provider attributes, and an electronic patient medical record database The present disclosure contemplates a computer-readable medium that includes instructions 22 or receives and executes instructions 22 responsive to a propagated signal, so that a device connected to a network 30 can communicate video, audio, images, text, or any other data over the network 30. Further, the instructions 22 may be transmitted or received over the network 30 via a communication interface 26. The communication interface 26 may be a part of the processor 12 or may be a separate component. The communication interface 26 may be created in software or may be a physical connection in hardware. The communication interface 26 is configured to connect with a network 30, external media, the display 16, or any other components in system 10, or combinations thereof. The connection with the network 30 may be a physical connection, such as a wired Ethernet connection or may be established wirelessly as discussed below. Likewise, the additional connections with other components of the system 10 may be physical connections or may be established wirelessly.

In an embodiment the instructions 22 may be operable when executed by the processor 12 to cause the system 10 to identify data indicative of an encounter.

The network 30 may include wired networks, wireless networks, or combinations thereof. The wireless network may be a cellular telephone network, an 802.11, 802.16, 802.20, or WiMax network. Further, the network 30 may be a public network, such as the Internet, a private network, such as an intranet, or combinations thereof, and may utilize a variety of networking protocols now available or later developed including, but not limited to TCP/IP based networking protocols.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a computer readable medium for execution by, or to control the operation of, data processing apparatus. While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding or carrying a set of instructions for execution by a processor or that cause a computer system to perform any one or more of the methods or operations disclosed herein. The computer readable medium can be a machine-readable storage device, a machine-readable storage substrate, a memory device, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

In a particular non-limiting, exemplary embodiment, the computer-readable medium can include a solid-state memory such as a memory card or other package that houses one or more non-volatile read-only memories. Further, the computer-readable medium can be a random access memory or other volatile re-writable memory. Additionally, the computer-readable medium can include a magneto-optical or optical medium, such as a disk or tapes or other storage device to capture carrier wave signals such as a signal communicated over a transmission medium. A digital file attachment to an e-mail or other self-contained information archive or set of archives may be considered a distribution medium that is a tangible storage medium. Accordingly, the disclosure is considered to include any one or more of a computer-readable medium or a distribution medium and other equivalents and successor media, in which data or instructions may be stored.

In an alternative embodiment, dedicated hardware implementations, such as application specific integrated circuits, programmable logic arrays and other hardware devices, can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

In accordance with various embodiments of the present disclosure, the methods described herein may be implemented by software programs executable by a computer system. Further, in an exemplary, non-limited embodiment, implementations can include distributed processing, component/object distributed processing, and parallel processing. Alternatively, virtual computer system processing can be constructed to implement one or more of the methods or functionality as described herein.

Although the present specification describes components and functions that may be implemented in particular embodiments with reference to particular standards and protocols, the invention is not limited to such standards and protocols. For example, standards for Internet and other packet switched network transmission (e.g., TCP/IP, UDP/IP, HTML, HTTP, and HTTPS) represent examples of the state of the art. Such standards are periodically superseded by faster or more efficient equivalents having essentially the same functions. Accordingly, replacement standards and protocols having the same or similar functions as those disclosed herein are considered equivalents thereof.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and anyone or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), or a tablet device, to name just a few. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a device having a display, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

The illustrations of the embodiments described herein are intended to provide a general understanding of the structure of the various embodiments. The illustrations are not intended to serve as a complete description of all of the elements and features of apparatus and systems that utilize the structures or methods described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

While this specification contains many specifics, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings and described herein in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

It is therefore intended that the foregoing detailed description be regarded as illustrative rather than limiting, and that it be understood that it is the following claims, including all equivalents, that are intended to define the spirit and scope of this invention.

What is claimed is:

1. One or more non-transitory computer storage media storing computer-useable instructions that, when used by one or more computing devices, cause the one or more computing devices to perform a method for visualizing patient conditions over time, the method comprising:
   generating a graphical user interface for display by a user computing device;
   identifying a plurality of encounters associated with a particular patient;
   organizing the plurality of encounters into one or more encounter groupings, wherein encounters of the plurality of encounters that are grouped into a particular encounter grouping share similar characteristics;
   generating at least one encounter indicator for each of the one or more encounter groupings, the at least one encounter indicator having a size, a color, and a halo:
      the size having a first size associated with a number of encounters in the encounter grouping;
      the color having a first color associated with a type of encounter of encounters in the encounter grouping; and
      the halo having a first width associated with the number of locations associated with the encounters in the encounter grouping;
   presenting the at least one encounter indicator for each of the one or more encounter groupings;
   identifying at least one new encounter associated with the particular user;
   responsive to identifying the at least one new encounter, updating at least one of the size, the color, or the halo of the at least one encounter indicator; and
   presenting the at least one encounter indicator as updated for the at least one of the size, the color, or the halo.

2. The one or more computer storage media of claim 1, wherein each of the plurality of encounters occurs within a specified timeframe, wherein the similar characteristics comprise an encounter type that is an outpatient clinical.

3. The one or more computer storage media of claim 1, wherein the similar characteristics further comprise a diagnosis associated with a body part of the particular patient, and wherein the encounters that are grouped into the particular encounter grouping are presented in a body map.

4. The one or more computer storage media of claim 1, wherein the similar characteristics further comprise a diagnosis based on a unified ontology or nomenclature, and wherein the interaction with the encounter indicator comprises hovering or selecting.

5. The one or more computer storage media of claim 1, wherein the similar characteristics are derived from one or more fields of an Electronic Health Record associated with the particular patient.

6. The one or more computer storage media of claim 1, wherein the locations associated with the encounters in the one or more encounter groupings are at least one of a primary care facility or an emergency care facility.

7. The one or more computer storage media of claim 1, wherein upon receipt of a selection of the encounter indicator, the method further comprises presenting additional information regarding the encounters represented thereby.

8. The one or more computer storage media of claim 1, wherein the method further comprises presenting a timeline, the timeline having a temporal indicator for each encounter represented by the encounter indicators for each of the one or more encounter groupings, the temporal indicators illustrating a relative time in which each of the plurality of encounters occurred.

9. The one or more computer storage media of claim 8, wherein the temporal indicators include a visual characteristic indicative of the encounter indicator that represents the one or more encounter groupings in which the temporal indicator is organized.

10. A method for visualizing patient conditions over time, the method comprising:
   generating a graphical user interface for display by a user computing device;
   identifying a plurality of encounters associated with a particular patient, each of the plurality of encounters is associated with a health-altering event and share similar characteristics;
   organizing the plurality of encounters into an encounter grouping;
   generating at least one encounter indicator for the encounter grouping, the at least one encounter indicator having a size, a color, and a halo:
      the size having a first size associated with a number of encounters in the encounter grouping;

the color having a first color associated with a type of encounter of encounters in the encounter grouping; and the halo having a first width associated with the number of locations associated with the encounters in the encounter grouping;

presenting the at least one encounter indicator for the encounter grouping; and identifying at least one new encounter associated with the particular user;

responsive to identifying the at least one new encounter, updating at least one of the size, the color, or the halo of the at least one encounter indicator; and presenting the at least one encounter indicator as updated for the at least one of the size, the color, or the halo.

11. The method of claim 10, wherein each of the plurality of encounters occurs within a specified timeframe.

12. The method of claim 10, wherein the at least one encounter indicator further comprises a shading extending around at least a portion of a perimeter of the encounter indicator, the shading correlating to the similar characteristics.

13. The method of claim 12, wherein the shading correlates to a type of encounter locations associated with the encounter grouping.

14. The method of claim 10, wherein the similar characteristics are derived from one or more fields of an Electronic Health Record associated with the particular patient.

15. The method of claim 10, wherein the locations associated with the encounters in the one or more encounter groupings are at least one of a primary care facility or an emergency care facility.

16. The method of claim 10, wherein upon receipt of a selection of the encounter indicator, the method further comprises presenting additional information regarding the plurality of encounters represented thereby.

17. The method of claim 10, further comprising presenting a timeline, the timeline having a temporal indicator for each encounter represented by the encounter indicators for each encounter grouping, the temporal indicators illustrating a relative time in which each of the plurality of encounters occurred.

18. The method of claim 17, wherein at least one of the temporal indicators includes a visual characteristic indicative of the encounter indicator that represents the encounter grouping in which the at least one of the temporal indicators is organized.

19. One or more non-transitory computer storage media storing computer-useable instructions that, when used by one or more computing devices, cause the one or more computing devices to perform a method for visualizing patient conditions over time, the method comprising:

generating a graphical user interface for display by a user computing device;

identifying a plurality of encounters associated with a particular patient, each of the plurality of encounters occurring in a particular timeframe;

organizing the plurality of encounters into a plurality of encounter groupings, wherein encounters that are organized in the same encounter grouping share a similar diagnosis;

generating at least one encounter indicator for each of the plurality of encounter groupings, the at least one encounter indicator having a size, a color, and a halo:

the size having a first size associated with a number of encounters in the encounter grouping;

the color having a first color associated with a type of encounter of encounters in the encounter groupings; and the halo having a first width associated with the number of locations associated with the encounters in the encounter grouping;

presenting the at least one encounter indicator for each of the plurality of encounter groupings;

identifying at least one new encounter associated with the particular user;

responsive to identifying the at least one new encounter, updating at least one of the size, the color, or the halo of the at least one encounter indicator; and presenting the at least one encounter indicator as updated for the at least one of the size, the color, or the halo.

20. The one or more computer storage media of claim 19, wherein the similar diagnosis shared by encounters that are organized in the same encounter grouping is derived utilizing a unified ontology or nomenclature.

* * * * *